(12) United States Patent
Gehlsen

(10) Patent No.: US 6,531,120 B2
(45) Date of Patent: Mar. 11, 2003

(54) OPHTHALMIC HISTAMINE COMPOSITIONS AND USES THEREOF

(75) Inventor: Kurt R. Gehlsen, Encinitas, CA (US)

(73) Assignee: Maxim Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 10/000,462

(22) Filed: Nov. 30, 2001

(65) Prior Publication Data

US 2002/0098224 A1 Jul. 25, 2002

Related U.S. Application Data

(63) Continuation of application No. PCT/US00/15379, filed on Jun. 2, 2000.
(60) Provisional application No. 60/137,564, filed on Jun. 3, 1999.

(51) Int. Cl.[7] .............................................. A61K 31/74
(52) U.S. Cl. ................................. 424/78.05; 424/78.04
(58) Field of Search ........................... 424/78.04, 78.05

(56) References Cited

U.S. PATENT DOCUMENTS

| | | |
|---|---|---|
| 4,510,145 A | 4/1985 | Schacher |
| 5,716,610 A | 2/1998 | Jack et al. |
| 5,800,807 A | 9/1998 | Hu et al. |
| 5,861,148 A | 1/1999 | Smith |
| 5,872,086 A | 2/1999 | Ellis et al. |
| 5,877,154 A | 3/1999 | Naveh et al. |
| 5,895,645 A | 4/1999 | Dabrowski et al. |
| 5,951,971 A | 9/1999 | Kawashima et al. |
| 6,270,781 B1 * | 8/2001 | Gehlsen ...................... 424/401 |

FOREIGN PATENT DOCUMENTS

| | | |
|---|---|---|
| WO | WO 95/13087 | 5/1995 |
| WO | WO 95/23601 | 9/1995 |
| WO | WO 97/44062 | 11/1997 |
| WO | WO 98/18458 | 5/1998 |
| WO | WO 99/25341 | 5/1999 |
| WO | WO 00/40240 | 7/2000 |

OTHER PUBLICATIONS

Joseph Price Remington, *Remington's Pharmaceutical Sciences*, (18th ed. 1990), Mack Publishing Co.
Ho–Wah Hui et al., *Ocular Disposition of Topically Applied Histamine, Cimetidine, and Pyrilamine in the Albino Rabbit*, Current Eye Research, vol. 3, No. 2, 1984 pp. 321–330, XP001010645.

* cited by examiner

Primary Examiner—Carlos Azpuru
(74) Attorney, Agent, or Firm—Knobbe, Martens, Olson & Bear, LLP

(57) ABSTRACT

An ophthalmic composition for use in reducing ocular irritation comprising histamine, at a concentration of between about 0.01 and 1.0% by weight, in a pharmaceutically acceptable carrier, adapted for ophthalmic administration.

12 Claims, No Drawings

OPHTHALMIC HISTAMINE COMPOSITIONS AND USES THEREOF

RELATED APPLICATIONS

This application is a continuation of International Application No. PCT/US00/15379 having international filing date of Jun. 2, 2000, designating the United States of America and published under PCT Article 21(2) in English, which claims the benefit of priority from Provisional Application No. 60/137,564, filed Jun. 3, 1999 each of which is hereby incorporated by reference in their entirety.

BACKGROUND OF THE INVENTION

Field of the Invention

The present invention relates to ophthalmic histamine-containing preparations for the treatment of ocular irritation. More precisely, the invention relates to an aqueous formulation of histamine or similar compounds, to be instilled in and around the eye as well as in the conjunctival sac to treat various forms of ocular irritation.

There are a number of patents that address various ophthalmic formulations to ease ocular irritation. For example, U.S. Pat. Nos. 5,895,645; 5,877,154; 5,872,086; and 5,861,148; each recite an ophthalmic solution formulated to ease ocular irritation. However, none of these patents discuss the use of histamine-containing formulations for the reduction of ocular irritation.

SUMMARY OF THE INVENTION

One embodiment of the present invention is an ophthalmic composition for use in reducing ocular irritation, comprising a compound selected from the group consisting of histamine, a histamine receptor analog, serotonin and a serotonin analog, and a pharmaceutically acceptable ophthalmic carrier. In one aspect of this embodiment, the histamine is histamine dihydrochloride or histamine phosphate. Preferably, the histamine is present at a concentration of between about 0.001% and 10% by weight. More preferably, the histamine is present at a concentration of between about 0.05% and 5% by weight. Most preferably, the histamine is present at a concentration of between about 0.1% and 1% by weight. In one aspect of this preferred embodiment, the pharmaceutically acceptable carrier is an aqueous solution, gel or ointment. Preferably, the aqueous solution has a pH of between about 6.8 and 7.6.

Another embodiment of the present invention provides a method for treating ocular irritation in a subject in need thereof, comprising administering to the subject an effective ocular irritation-reducing amount of an ophthalmic composition comprising a compound selected from the group consisting of histamine, a histamine receptor analog, serotonin and a serotonin analog, and a pharmaceutically acceptable ophthalmic carrier. In one aspect of this embodiment, the histamine is histamine dihydrochloride or histamine phosphate. Advantageously, the subject is a human. In one aspect of this embodiment, the ocular irritation is caused by exposure to a pollutant, chemical compound, dust particles, ultraviolet light or a pathogen. The pathogen can be, for example, a virus or bacterium. In one aspect of this embodiment, the virus is a herpes virus. In another aspect of this embodiment, the bacterium is *Neisseria gonorrhea*. The ocular irritation can be caused by, for example, laser in situ keratomileusis (LASIK), radial keratotomy (RK), photo refractive keratectomy (PRK) or cataract surgery, or an allergic reaction. The compositions described herein can be administered by spraying into the eye, application of an ophthalmic gel or eye drops. Preferably, 1–2 drops of the composition is administered per eye, between 4 and 8 times per day.

Another embodiment of the present invention is a composition comprising a compound selected from the group consisting of histamine, a histamine receptor analog, serotonin and a serotonin analog, and a pharmaceutically acceptable ophthalmic carrier for use in reducing ocular irritation in a subject. In one aspect of this embodiment, the histamine is histamine dihydrochloride or histamine phosphate. The ophthalmic carrier is preferably an aqueous solution, gel or ointment. Preferably, the histamine is present at a concentration of between about 0.001% and 10% by weight. More preferably, the histamine is present at a concentration of between about 0.05% and 5% by weight. Most preferably, the histamine is present at a concentration of between about 0.1% and 1% by weight.

Another embodiment of the present invention provides the use of a composition comprising a compound selected from the group consisting of histamine, a histamine receptor analog, serotonin and a serotonin analog, and a pharmaceutically acceptable ophthalmic carrier for reducing ocular irritation in a subject. In one aspect of this embodiment, the histamine is histamine dihydrochloride or histamine phosphate. Preferably, the histamine is present at a concentration of between about 0.001% and 10% by weight. More preferably, the histamine is present at a concentration of between about 0.05% and 5% by weight. Most preferably, the histamine is present at a concentration of between about 0.1% and 1% by weight.

DETAILED DESCRIPTION OF THE PREFERRED EMBODIMENTS

The present invention relates to the use of ophthalmic pharmaceutical formulations comprising histamine for reducing ocular irritation. Ocular irritation can result from various ophthalmic surgical procedures, contact lens wear, exposure to allergens, ocularly irritating chemical compounds, pollutants, dust particles, ultraviolet light, and various pathogenic agents that cause conjunctivitis, including various infections of the eye such as herpetic infections, other viral infections, and bacterial infections. Surprisingly, ophthalmic administration of histamine-containing formulations is effective to reduce ocular irritation.

The histamine-containing formulations described herein preferably comprise histamine dihydrochloride, however, other forms of histamine, such as histamine phosphate, as well as histamine receptor analogs, serotonin and serotonin analogs are also contemplated for use in the present invention.

The histamine is present in the pharmaceutical formulations in an amount effective to reduce ocular irritation. The concentration of histamine, or a similarly functioning compound, in the formulations described herein is expressed in terms of percent histamine by weight of the total composition. For example, in one embodiment, histamine is present in an amount between about 0.001 and 10 percent by weight. In another embodiment, histamine is present in an amount between about 0.05 and 5 percent by weight. In still another embodiment, histamine is present in an amount of between about 0.1 and 1 percent by weight.

The formulations described herein comprise histamine and a pharmaceutically acceptable carrier. In a preferred embodiment, the carrier is a sterile, aqueous solution that is buffered with compounds such as phosphate buffers, carbonate buffers and the like. The composition is preferably provided as a buffered aqueous solution having a viscosity of from about 1 to 50 centipoise (cps). In another preferred embodiment, the composition is formulated as a viscous liquid having a viscosity of between about 50 and several thousand cps using viscosity-enhancing agents such as, for example propylene glycol, hydroxymethyl cellulose or glycerin.

Other ophthalmic histamine-containing pharmaceutical carriers are also contemplated, including, for example, gels and ointments. The formulations can also comprise ingredients which regulate the osmolarity of the final formulation, as well as the pH of the formulations.

For example, the resulting preparations for ocular use are advantageously hypotonic, and have an osmolarity of between about 140 and 280 mOsm/l, and a pH of between about 6.8 and 7.6. The osmolarity of the solutions can be adjusted by means of well known osmolarity adjusting agents such as sodium chloride, potassium chloride and monosaccharides. Alternatively, the resulting preparations can be isotonic, or in another embodiment, the resulting preparations can be hypertonic. The present formulations may also contain other conventional ingredients used in ophthalmic preparations, such as dextrose, preservatives (e.g. Thimerosal™, i.e., sodium ethylmercurithiosalicylate (Sigma; St. Louis, Mo.), benzalkonium chloride), corticosteroids (e.g. prednisone), analgesics (e.g., ibuprofen), antibiotics (e.g., gentamicin, streptomycin), antioxidants (e.g. ascorbic acid, BHA, BHT), demulcents (e.g., glycerin, propylene glycol), and the like. Descriptions of compounds used in standard ophthalmic formulations may be found in, for example, *Remington's Pharmaceutical Sciences,* latest edition, Mack Publishing Co. Easton, Pa., and in U.S. Pat. Nos. 5,951,971, 5,861,148, and 5,800,807.

The pH of the formulations described herein can be adjusted to the desired value by adding an acid, such as hydrochloric acid, or a base such as sodium hydroxide, until the pH of the formulation falls within the range described above. Such adjustments are preferably made without increasing the ionic strength of the formulation to beyond acceptable levels.

The present histamine-containing compositions are prepared according to conventional techniques by mixing the relative ingredients in appropriate amounts in sterile water, or preparing histamine-containing gels and ointments using gel and ointment preparation techniques well known in the pharmaceutical arts. In preferred embodiments, the formulations are sterilized prior to use.

The ophthalmic formulations described herein are administered to the eyes of a subject, preferably an animal such as a dog, cat, bird, reptile or amphibian, more preferably a mammal, most preferably a human, by any route and through any means where delivery of the histamine content of the formulation to the site of ocular irritation can be achieved. For example, the formulations are administered by spray, by ophthalmic gel, by eye drop, by injection within the eye, or by other methods of administration well known to those of skill in the relevant art. In one embodiment of the present invention, daily dosages in human therapy of the present ophthalmic formulations are of about 1–2 drops per eye, administered about 1–8 times a day (for instance by means of a standard pharmacopeial medicinal dropper of 3 mm in external diameter, which when held vertically delivers 20 drops of water of total weight of 0.9-1-1 grams at 25° C.)

The formulations described herein can be used to reduce ophthalmia or eye inflammation resulting from contact lens wear, or conditions such as uveitis, iritis, allergic reactions such as severe hay fever, watery eyes, conjunctivitis such as ocular bacterial infections and ocular viral infections. Various forms of conjunctivitis include: gonococcal conjunctivitis, a form of conjunctivitis caused by the bacterium *Neisseria gonorrhea,* Inclusion Conjunctivitis, a form of conjunctivitis caused by the bacterium *Chlamydia trachomatis,* vernal keratoconjunctivitis, keratoconjunctivitis sicca, episcleritis, scleritis, and the like.

Conjunctivitis or inflammation of the conjunctiva can be caused by a number of factors including an allergic reaction to dust, mold, animal dander, pollen, or other allergens, and can be irritated by wind, dust, smoke, and other types of air pollution. The conjunctiva may also be irritated by a common cold or a bout of measles. The ultraviolet light of an electric welding arc, sunlamp, or even bright sunlight reflected by snow or water can irritate the conjunctiva. Conjunctivitis can also be caused by problems with the tear ducts, sensitivity to chemicals, exposure to irritants, and infection by particular bacteria—typically chlamydia. Conjunctivitis can last for months or years.

When irritated, the conjunctiva becomes bloodshot, and a discharge often appears in the eye. In bacterial conjunctivitis, the discharge may be thick and white or creamy. In viral or allergic conjunctivitis, the discharge is usually clear. The eyelid may swell and itch intensely, especially in allergic conjunctivitis.

Usually conjunctivitis is easy to recognize because it commonly occurs with a cold or allergies. Sometimes, however, conjunctivitis resembles iritis, a more severe eye inflammation, or even acute glaucoma—serious conditions that can lead to a loss of vision. A doctor can usually distinguish the diseases. With the more serious eye conditions, the blood vessels closest to the colored part of the eye (iris) are very inflamed. Although conjunctivitis may cause a burning sensation, it is usually less painful than the more serious conditions. Conjunctivitis almost never affects vision unless the discharge temporarily covers the cornea.

The formulations described herein can also be used to reduce ocular irritation caused by a variety of ocular surgical techniques including LASIK, PK, PRK, and cataract surgery.

EXAMPLES

Particular aspects of the invention can be more readily understood by reference to the following examples, which are intended to exemplify the invention, without limiting its scope to the particular embodiments.

Example 1

Treatment of Watery Eyes Caused by Exposure to an Allergen

A subject exposed to an allergen and presenting ocular irritation as a result is administered an aqueous histamine-containing formulation containing 0.01% histamine dihydrochloride by weight. The subject is administered 2 drops per eye every three hours or as necessary to relieve the ocular irritation.

Example 2

Treatment of Watery Eyes Caused by Exposure to a Pollutant

A subject exposed to a pollutant and presenting ocular irritation as a result is administered an aqueous histamine-containing formulation containing 0.1% histamine dihydrochloride by weight. The subject is administered 4 drops per eye every three hours or as necessary to relieve the ocular irritation.

Example 3

Treatment of Watery Eyes Caused by Contact Lens Wear

A subject presenting ocular irritation as a result of contact lens wear is administered an aqueous histamine-containing formulation containing 0.05% histamine dihydrochloride by weight. The subject is administered 2 drops per eye every three hours or as necessary to relieve the ocular irritation.

Example 4

Gonococcal Conjunctivitis

Gonococcal conjunctivitis is a gonococcal infection of the eye. Newborns can acquire a gonococcal infection of the conjunctiva from their mother while passing through the birth canal. For this reason, most states require that all newborns receive eyedrops—often silver nitrate, povidone iodine, or an antibiotic ointment such as erythromycin—to kill the bacteria that could cause gonococcal conjunctivitis. Adults can contract gonococcal conjunctivitis during sexual activity if, for example, infected semen gets into the eye. Usually only one eye is involved.

Within 12 to 48 hours after the infection starts, the eye becomes red and painful. If the infection isn't treated, ulcers can form on the cornea, an abscess can develop, the eyeball can become perforated, and even blindness can result.

A subject presenting the symptoms of gonococcal conjunctivitis is treated with a histamine-containing spray formulation with 0.05% histamine dihydrochloride by weight and also containing antibiotics effective against gonorrhea. The spray is administered to the subject 2 times per day for four to six weeks.

Example 5

Trachoma

Trachoma (granular conjunctivitis, Egyptian ophthalmia) is a prolonged infection of the conjunctiva caused by the bacterium *Chlamydia trachomatis*. Trachoma is common in poverty-stricken parts of the dry, hot Mediterranean countries and the Far East. It occurs occasionally among Native Americans and among people in mountainous areas of the southern United States. Trachoma is contagious in its early stages and may be transmitted by eye-hand contact, by certain flies, or by contaminated articles such as towels and handkerchiefs.

In the early stages of the disease, the conjunctiva is inflamed, reddened, and irritated, and a discharge appears. In the later stages, the conjunctiva and cornea become scarred, causing the eyelashes to turn inward and vision to become impaired.

A subject diagnosed with trachoma is administered three times daily a histamine-containing formulation of the present invention in the form of an ophthalmic gel containing 0.02% by weight histamine phosphate and tetracycline or erythromycin for 4 to 6 weeks.

Example 6

Photo Refractive Keratectomy (PRK)

Photo refractive keratectomy (PRK) is the sculpting of a myopic or hyperopic lens for refractive reasons on the front surface of the eye with the use of a "cold" laser light. Utilizing the accuracy and precision of the excimer laser, PRK changes the shape of the cornea to improve the refraction of a subject's eyes.

A subject having received PRK is treated with a histamine-containing formulation in the form of eyedrops containing 0.025% histamine phosphate. The subject applies 2 drops four times daily to each eye for up to five weeks to reduce ophthalmic irritation caused by the PRK procedure.

Example 7

Radial Keratotomy (RK)

Radial keratotomy (RK) is a surgical procedure that changes the shape of the front of the eye with microscopic incisions oriented in a "radial" or spoke-like pattern around the outside of the cornea. This procedure, and a variation of RK called astigmatic keratotomy (AK) can reduce or eliminate nearsightedness and astigmatism by flattening the cornea. This allows light to focus more directly on the retina.

A subject who has recently received RK is treated with a histamine-containing formulation of the present invention in the form of eyedrops with histamine dihydrochloride at a final concentration of 0.2% by weight. The subject applies 2 drops four times daily for three weeks to each eye to reduce ophthalmic irritation caused by the RK procedure.

Example 8

Laser in Situ Keratomileusis (LASIK)

LASIK is a surgical operation for the treatment of refractive errors by reshaping tissue beneath the surface of the cornea. With LASIK, a flap of surface cornea is cut and rolled aside in order that a laser beam can remove internal tissue from the inside (stroma or body) of the cornea. Once the flap has been created the excimer laser is used to reshape the cornea underneath the flap. Following removal of tissue the surface layer is reattached. The amount and shape of the removed tissue is determined by the preoperative refractive error i.e. myopia, hyperopia or astigmatism.

A subject who has recently received LASIK is treated with a histamine-containing formulation of the present invention in the form of a spray. The spray contains 0.5% histamine dihydrochloride by weight. The subject applies 2 sprays of the formulation four times daily to each eye for six weeks to reduce ophthalmic irritation caused by the LASIK procedure.

While particular embodiments of the invention have been described in detail, it will be apparent to those of skill in the relevant art that these embodiments are exemplary, rather than limiting. The true scope of the invention is that defined within the attached claims and equivalents thereof. All references cited herein are hereby expressly incorporated by reference.

What is claimed is:

1. An ophthalmic composition for use in reducing ocular irritation comprising a compound selected from the group consisting of histamine or a histamine receptor analog, and a pharmaceutically acceptable ophthalmic carrier, wherein the carrier is a gel.

2. The composition of claim 1, wherein said histamine is histamine dihydrochloride or histamine phosphate.

3. A method for treating ocular irritation in a subject in need thereof, comprising administering to said subject an effective ocular irritation-reducing amount of an ophthalmic composition comprising a compound selected from the group consisting of histamine or a histamine receptor analog, and a pharmaceutically acceptable ophthalmic carrier, wherein the carrier is a gel.

4. The method of claim 3, wherein said histamine is histamine dihydrochloride or histamine phosphate.

5. The method of claim 3, wherein said subject is a human.

6. The method of claim 3, wherein said ocular irritation is caused by exposure to an agent selected from the group consisting of a pollutant, chemical compound, dust particles, ultraviolet light and pathogen.

7. The method of claim 3, wherein said pathogen is selected from the group consisting of a virus and a bacterium.

8. The method of claim 7, wherein said virus is a herpes virus.

9. The method of claim 7, wherein said bacterium is *Neisseria gonorrhea*.

10. The method of claim 3, wherein said ocular irritation is caused by an ophthalmic surgical technique selected from the group consisting of laser in situ keratomileusis (LASIK), radial keratotomy (RK), photo refractive keratectomy (PRK), and cataract surgery.

11. The method of claim 3, wherein said ocular irritation is caused by an allergic reaction.

12. The method of claim 3, wherein said composition is in solution and said administering comprises administering 1–2 drops of said composition per eye, between 4 and 8 times per day.

* * * * *